(12) United States Patent
Cambronne et al.

(10) Patent No.: US 11,020,582 B2
(45) Date of Patent: Jun. 1, 2021

(54) INTRAVASCULAR PUMP WITH EXPANDABLE REGION

(71) Applicant: Cardiovascular Systems, Inc., St. Paul, MN (US)

(72) Inventors: Matthew D. Cambronne, North Oaks, MN (US); Joseph P. Higgins, Minnetonka, MN (US); Tristan A. Van de Moortele, Minneapolis, MN (US); Matthew W. Tilstra, Rogers, MN (US); Jeffrey R. Stone, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 138 days.

(21) Appl. No.: 16/388,457

(22) Filed: Apr. 18, 2019

(65) Prior Publication Data
US 2019/0321531 A1 Oct. 24, 2019

Related U.S. Application Data

(60) Provisional application No. 62/660,511, filed on Apr. 20, 2018.

(51) Int. Cl.
| *A61M 60/135* | (2021.01) |
| *A61F 2/82* | (2013.01) |
| *A61M 60/205* | (2021.01) |
| *A61M 60/894* | (2021.01) |

(52) U.S. Cl.
CPC .............. *A61M 60/135* (2021.01); *A61F 2/82* (2013.01); *A61M 60/205* (2021.01); *A61M 60/894* (2021.01); *A61F 2210/0014* (2013.01); *A61F 2250/001* (2013.01)

(58) Field of Classification Search
None
See application file for complete search history.

(56) References Cited

U.S. PATENT DOCUMENTS

| 2003/0187322 | A1 | 10/2003 | Siess |
| 2004/0044266 | A1 | 3/2004 | Siess et al. |
| 2011/0004046 | A1 | 1/2011 | Campbell et al. |
| 2012/0041254 | A1 | 2/2012 | Scheckel |
| 2013/0303831 | A1 | 11/2013 | Evans |
| 2016/0136343 | A1 | 5/2016 | Anagnostopoulos |
| 2018/0055979 | A1 | 3/2018 | Corbett et al. |

OTHER PUBLICATIONS

International Search Report and Written Opinion issued in related PCT application No. PCT/US2019/028243, dated Jul. 3, 2019.
International Preliminary Report on Patentability issued by WIPO in related PCT application No. PCT/US2019/028243, dated Oct. 20, 2020.

*Primary Examiner* — Paula J Stice
(74) *Attorney, Agent, or Firm* — Barnes & Thornburg LLP; Jeffrey R. Stone

(57) ABSTRACT

The present invention provides an intravascular blood pump comprising an expandable and collapsible region distal to a pump assembly and proximal in certain embodiments to inlet apertures in the pump housing. In some embodiments, the expandable and collapsible region may comprise expandable and collapsible proximal and/or distal transition sections adjacent a central expandable and collapsible region. Support structure, e.g., an expandable and collapsible stent may comprise at least a part of the expandable and collapsible region.

15 Claims, 8 Drawing Sheets

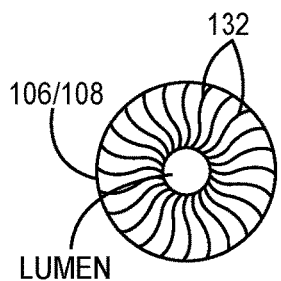
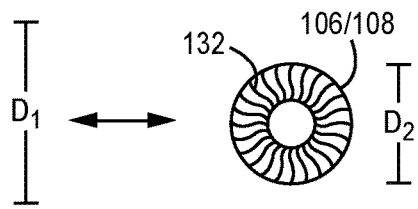
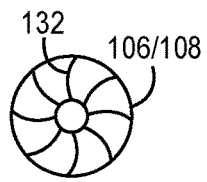
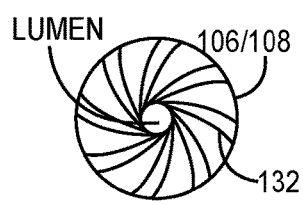
FIG. 10A  FIG. 10B  FIG. 10C  FIG. 10D
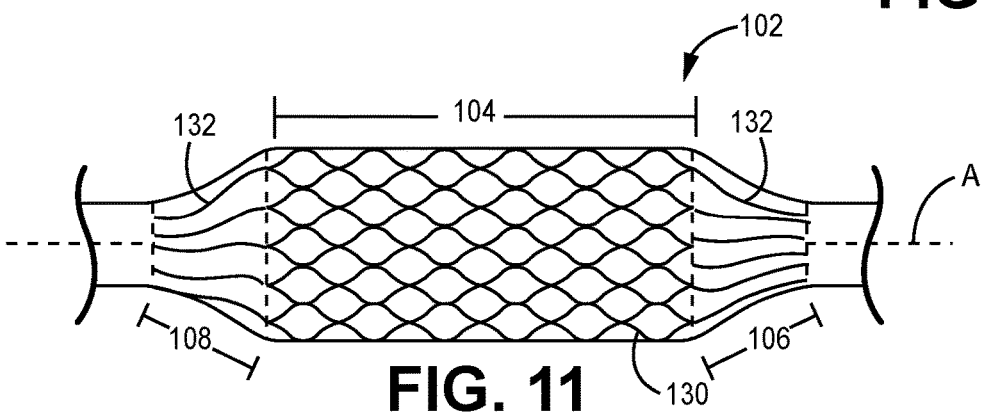
FIG. 11
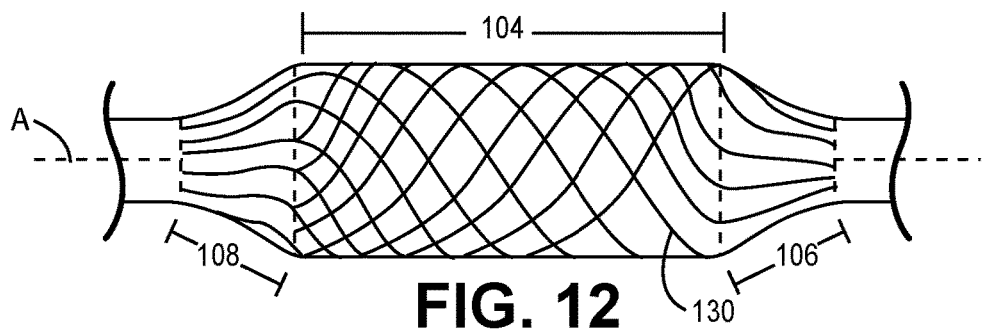
FIG. 12
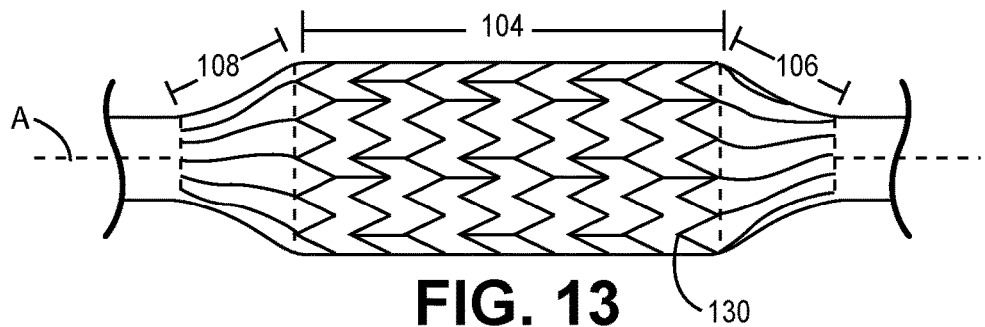
FIG. 13

INTRAVASCULAR PUMP WITH EXPANDABLE REGION

CROSS-REFERENCE TO RELATED APPLICATIONS

This application claims the benefit of provisional application 62/660,511, filed Apr. 20, 2018 and entitled INTRAVASCULAR BLOOD PUMP WITH EXPANDABLE REGION, the contents of which are hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular pump with an expandable region disposed distal to the impeller assembly.

Description of the Related Art

With reference to FIG. 1, the human heart comprises four chambers and four heart valves that assist in the forward (antegrade) flow of blood through the heart. The chambers include the left atrium, left ventricle, right atrium and left ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a stationary inducer, also known as a flow straightener; a rotational impeller; and a stationary diffuser and/or outflow structure; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the stationary inducer 6 before being urged forward by the rotating impeller 8. The blood flow may then be modified by a stationary diffuser and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a stationary inducer or flow straightener encountered by blood upon entry into the pump which can contribute to, inter alia, thrombosis and/or hemolysis.

Various embodiments of the present invention address these, inter alia, issues.

The figures and the detailed description which follow more particularly exemplify these and other embodiments of the invention.

BRIEF DESCRIPTION OF THE SEVERAL VIEWS OF THE DRAWINGS

FIG. 10A is an end view of one embodiment of the present invention;
FIG. 10B is an end view of one embodiment of the present invention;
FIG. 10C is an end view of one embodiment of the present invention;
FIG. 10D is an end view of one embodiment of the present invention;
FIG. 11 is a side cutaway view of one embodiment of the present invention;
FIG. 12 is a side cutaway view of one embodiment of the present invention;
FIG. 13 is a side cutaway view of one embodiment of the present invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 1:
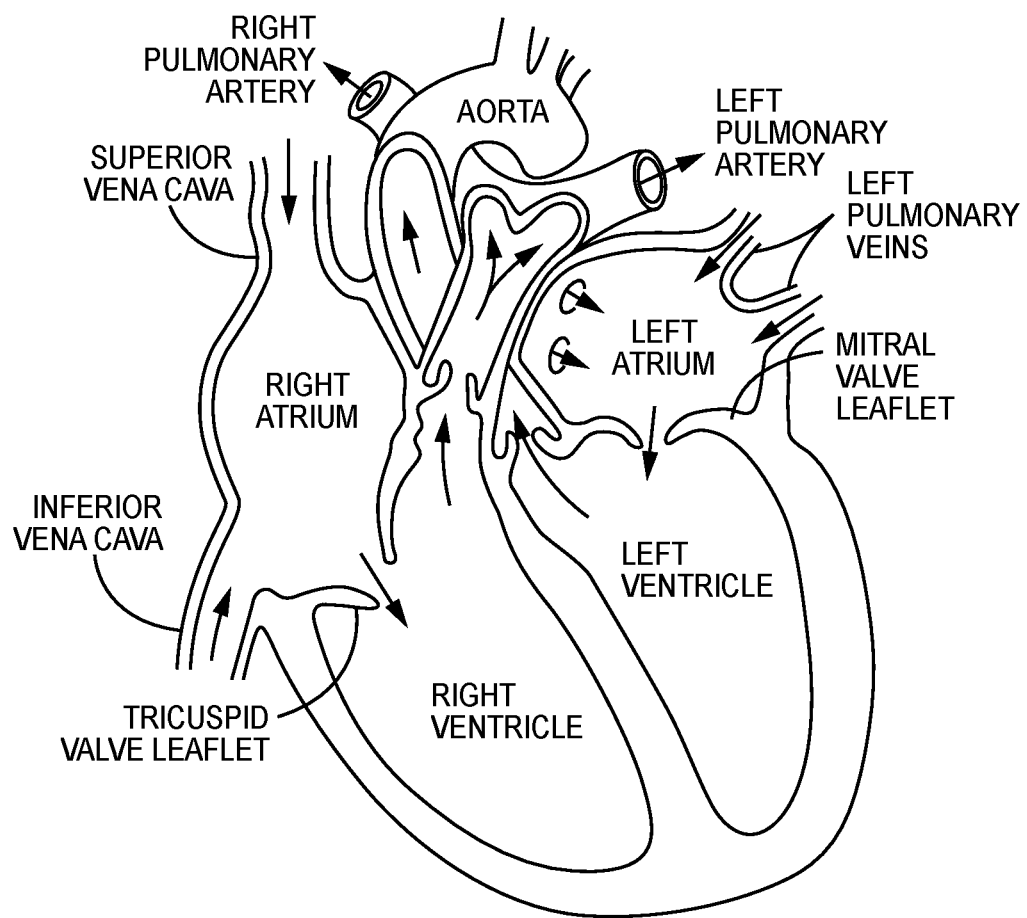
FIG. 1 is a cutaway view of the human heart.
Figure 2:
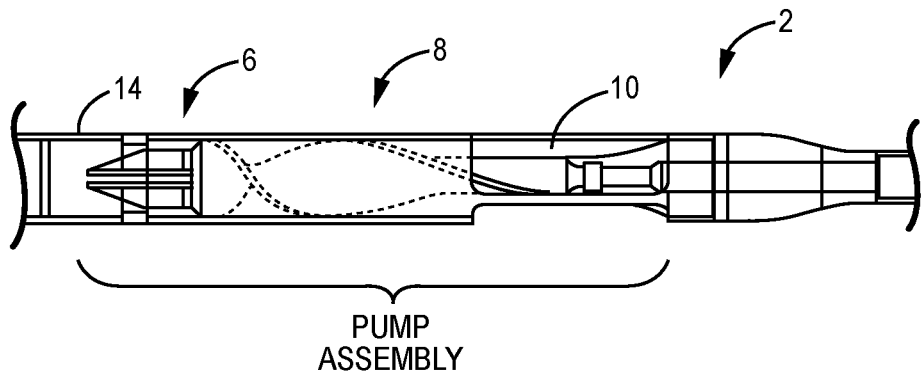
FIG. 2 is a cross-sectional view of a prior art device.
Figure 3:
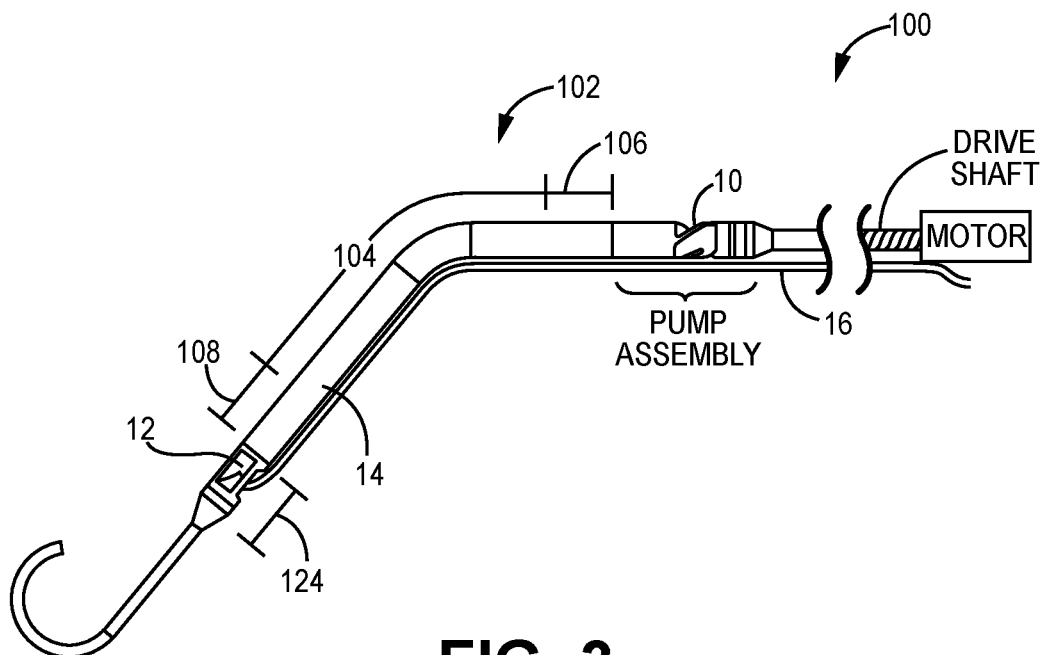
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 or pump assembly. The configuration shown in FIG. 3 may comprise a delivery configuration with an expandable region 102 compressed within an introducer or delivery sheath or catheter 200 (See FIGS. 9, 13A and 16-19).

With reference generally to the Figures, the device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Figure 4:
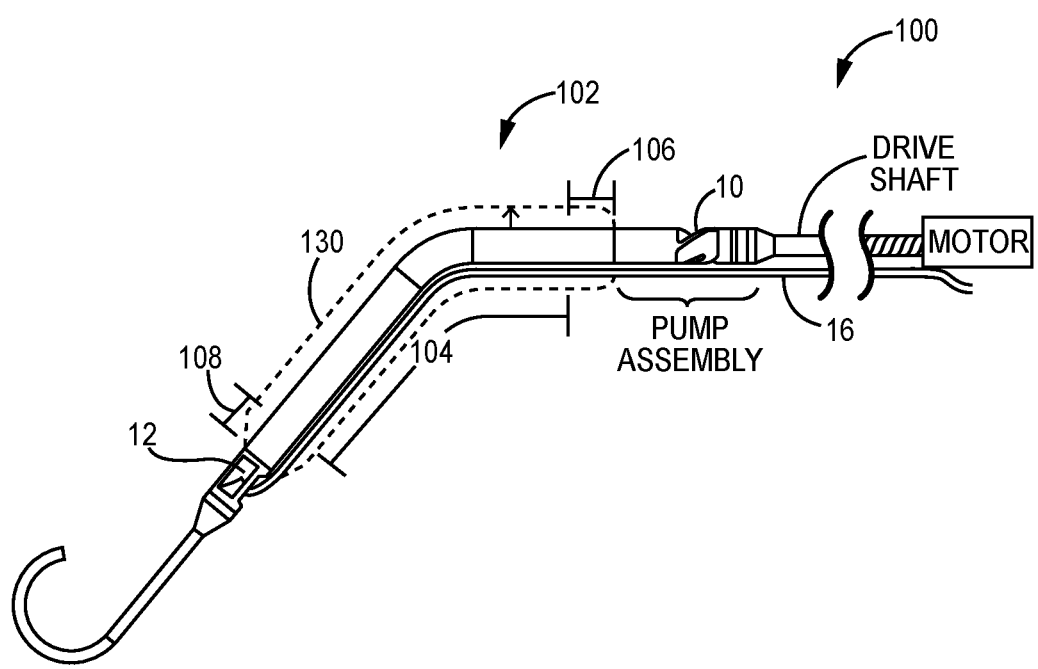
FIG. 4 is a side cutaway view of one embodiment of the present invention.

Thus, FIG. 4 shows device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4 as well as the remaining Figures, the device 100 comprises an expandable region 102 (shown in dashed lines) that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other support structure materials may comprise gold, tantalum, stainless steel, alloys such as aerospace alloys and/or polymers including but not limited to polymers that expand and contract upon exposure to relative heat and cold. In other cases, at least a portion of the expandable region 102, e.g, a central expandable section 104 discussed infra, may comprise a polymeric or other material sleeve that is configured to allow and/or accommodate expansion and collapsing and a support structure 130 may be omitted. FIGS. 3 and 4 provide a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor.

Further the support structure 130, when present, may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

As illustrated in the Figures, the expandable region 102 may comprise a proximal transition section 106 and/or a distal transition section 108. These transition section(s) 106, 108 provide an increasing diameter transition from the substantially fixed diameter non-expandable proximal and/or distal regions 122, 124 to the largest diameter of the expandable diameter region 102, achieved when undeformed and fully expanded.

Thus, in cross-sectional profile, the transition section(s) 106, 108 may comprise the shape and profile of a truncated or partial cone, though alternate profile shapes may also be employed. In one embodiment, the proximal transition section 106 may, therefore, comprise a diameter that increase in the distal direction and the distal transition section 108 may comprise a diameter that decreases in the distal direction. In these embodiments, the proximal transition section 106 will abut or is adjacent to the distal end of the proximal non-expandable region 122 and the distal transition section 108 abuts or is adjacent to the proximal end of the distal non-expandable region 124. The transition section(s) 106, 108 may be fixed to the adjacent non-expandable region(s) 122, 124 or one or both of the transition sections 106, 108 may be operatively connected to the adjacent non-expandable region in a way that allows a degree of relative rotation therebetween. The transition sections 106, 108 of this embodiment comprise a profile slope that is between 0 and 90 degrees, wherein the profile slope of the proximal transition section 106 may be substantially equal to the profile slope of the distal transition section 108 or the profile slopes of the proximal and distal transition sections 106, 108 may differ from each other.

Figure 5:
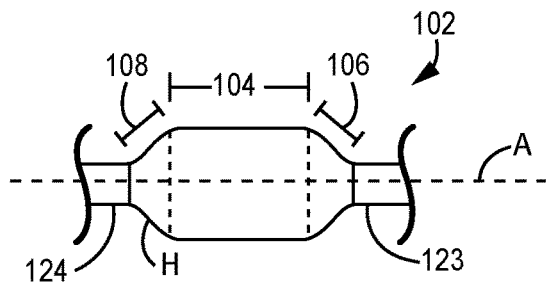
FIG. 5 is a side cutaway view of one embodiment of the present invention.
Figure 6:
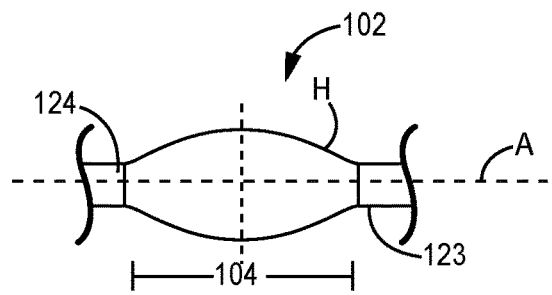
FIG. 6 is a side cutaway view of one embodiment of the present invention.

The central expandable section 104 may, as shown in FIG. 5, comprise a cylindrical shape or, as in FIG. 6, an elliptical shape. These shapes are merely exemplary.

Figure 7:
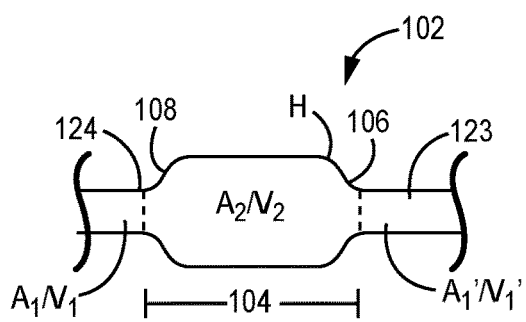
FIG. 7 is a side cutaway view of one embodiment of the present invention.
Figure 8:
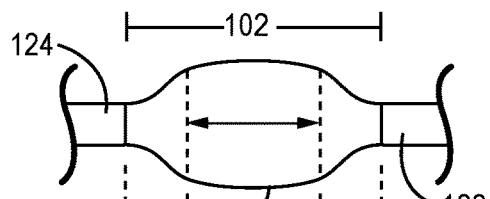
FIG. 8 is a side cutaway view of one embodiment of the present invention.
Figure 9:
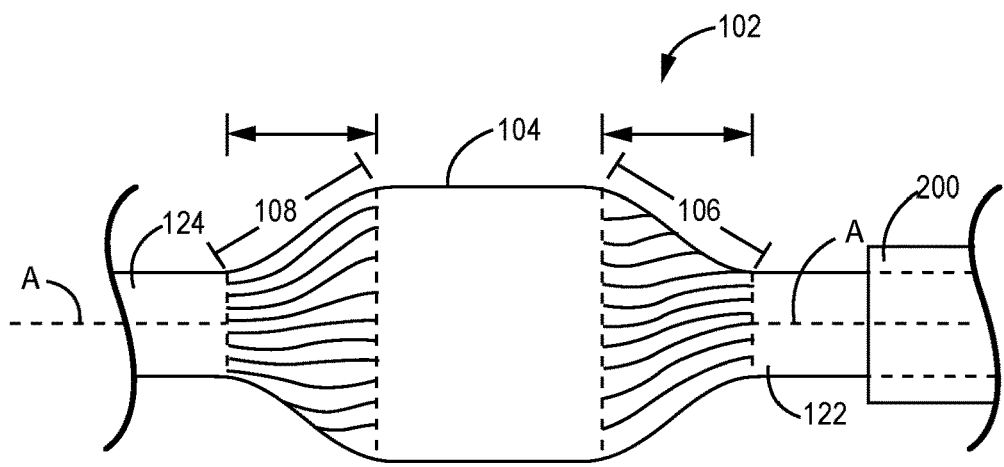
FIG. 9 is a side cutaway view of one embodiment of the present invention.

The expandable region 102, disposed just proximal to the inlet region comprising inlets 12 and just distal to the pump assembly is desirable because of the changes to the fluid flow that occur as a result. FIG. 7 illustrates the general principle wherein the incoming blood flows through the distal non-expandable region 124 of fixed diameter and, therefore, fixed area and volume and wherein the following relationships apply:

A=area and V=Volume, wherein $A_1/V_1 < A_2/V_2 > A_1'/V_1'$.

Because the expandable region 102 in FIG. 7 is larger in diameter than the distal non-expandable region 124, the area and volume are also larger, wherein the expandable region 102 is substantially filled with inflowing blood. Subjecting the blood flowing from the expandable region 102 to the smaller fixed diameter, area and volume provided by the proximal non-expandable area 122 results in a higher velocity flow rate at a point that is just distal to the impeller assembly 120. Various embodiments may comprise $A_1'/V_1'$ being roughly equivalent to $A_1/V_1$; or $A_1'/V_1'$ roughly equivalent to $A_2/V_2$; or $A_1'/V_1'$ less than $A_2/V_2$, but greater than $A_1/V_1$.

Figure 14A:
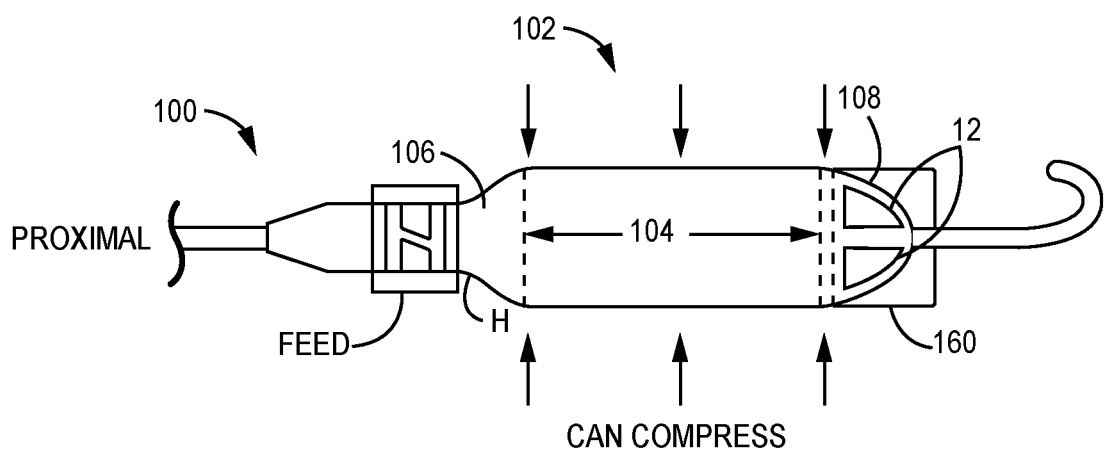
FIG. 14A is a side cutaway view of one embodiment of the present invention.
Figure 15A:
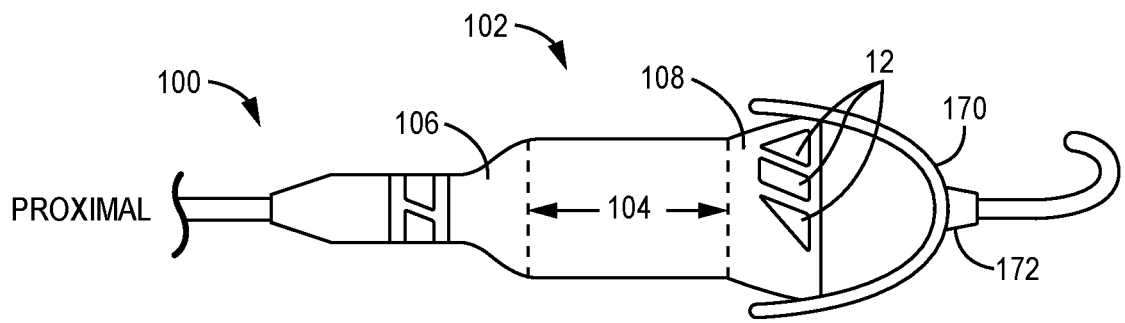
FIG. 15A is a side cutaway view of one embodiment of the present invention.
Figure 15B:
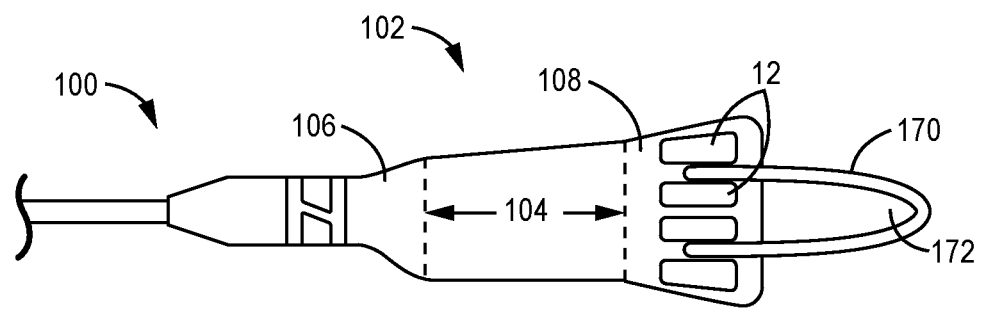
FIG. 15B is a side cutaway view of one embodiment of the present invention.
Figure 16:
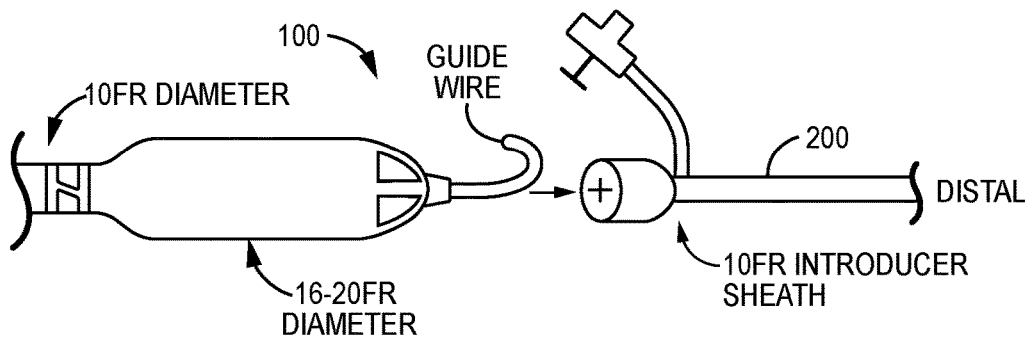
FIG. 16 is a side cutaway view of one embodiment of the present invention.

FIGS. 14A, 15A-15B provide an expandable region 102 that comprises a proximal transition section 106 as described above and wherein the expandable region 102 extends distally to include inlet apertures 12. Moreover, as in FIGS. 15A-15B, the distal transition section 108 comprises an expanded and enlarged diameter compared with the more proximal portions of expandable region 102.

In certain embodiments of the proximal and/or distal transition sections 106, 108 may comprise a support structure 130 comprising a series of non-linear, but uniformly non-linear, connecting structures 132 comprising, e.g., interconnected stent cells, and or wire struts, that may comprise a geometry that assists in the efficient collapsing of the expandable region 102 to a predictable collapsed configuration that is the smallest possible form without unpredicted interaction between the stent cells or wire struts in the transition sections 106, 108. Accordingly, as shown in FIGS. 9-13, the connecting structures comprising wires or struts 130 in the transition regions 106, 108 may be arranged in a swirl or spiral, or other complementary geometric pattern to allow easy expansion and collapsing, with maximum expansion and minimum collapsing, wherein the struts comprise complementary geometric shapes with smooth peaks and valleys that allow relatively close nesting together of adjacent struts when collapsed or crimped together. In this arrangement, the transition section struts or wires 132 will, upon application of a collapsing or crimping force that overcomes the prevalent biasing expansion force, begin to collapse.

The complementary and/or nesting geometry of the connecting structures 132 enables adjacent connecting structures 132 to collapse against each other in a nested configuration to provide the lowest collapsed profile possible and one with high predictability. This is best seen in FIG. 10A, showing an end view of an expanded transition section 106 or 108 with an expanded diameter $D_1$, and FIG. 10B showing a nested collapsed transition section with the connecting structures 132 comprising complementary shapes that fit or nest together to provide the smallest collapsed diameter $D_2$ possible. In some cases, the entire expandable region 102, including both transition sections 106, 108 and the central expandable section 104 may rotate slightly to accommodate the collapsing process as indicated by the arrow below. FIG. 10C illustrates another complementary shaping for the connecting structures 132, comprising a curved or curvilinear shape. FIG. 10D provides another complementary shaping for connecting structures 132, wherein the structures 132 are substantially straight or linear, but are arranged at an angle α relative to the housing defining the lumen and the larger diameter expandable region 102, wherein angle α may be a value greater than 0 degrees up to 90 degrees.

In a particularly preferred embodiment, the connecting structures 132 of the transition section(s) 106, 108 collapse and expand substantially concentrically about a central axis A with a substantially symmetrical profile in both the collapsed and expanded configurations, without relative rotation between the transition sections 106, 108, the central expandable region 104 and either non-expandable region 122, 124.

Further, the central expandable section 104 may comprise a plurality of pairs of interconnected wires wherein the first wire of the pair comprises undulations with peaks and valleys and the second wire of the pair comprises undulations with peaks and valleys but that are substantially opposed to the peaks and valleys of the first wire of the pair. See, e.g., FIGS. 11 and 12. The distal transition section 108 may then be formed from a first wire of the pair of wires of the central section 104 and the proximal transition section 106 may be formed from a second wire of the pair of wires of the central section 104. Alternatively, both transition sections 106, 108 may both be formed from the first or second wire of the central section 104.

With the additional exemplary support structure 130 comprising a zig-zag stent cell construction, with connecting struts as shown in FIG. 12, the skilled artisan will now readily recognize alternative and equivalent embodiments for the support structure 130, each of which is within the scope of the present invention.

Still more alternatively, the embodiment comprising a central stent cell structure, as in FIGS. 11-13, may be connected with the proximal and/or distal transition connection structures 132 but in a way that allows the expandable central section 104 and/or proximal and/or distal transition structure(s) 106, 108 a degree of rotational independence from each other to, inter alia, assist in accommodating the expansion and collapsing discussed herein. As discussed above, a preferred embodiment does not require such rotational independence.

In the embodiment where the proximal and distal transition sections 106, 108 both comprise connecting structure 132 geometry that collapses to nest as described herein but with a degree of rotation, the central expandable section 104 may also rotate generally in the same rotational direction as the transition structures when collapsing and expanding. Thus, the entire expandable region 102 of the device may comprise a collapsed rotational position having a first rotational angle, and an expanded rotational position with a second rotational angle that differs from the first rotational angle of the collapsed rotational position. In this case, the expandable region 102 may rotate independently of, and relative to, the position of the proximal and/or distal non-expandable regions 122, 124 of the device.

It is also contemplated that the central expandable section 102 may rotate as described above as the proximal and distal transition sections 106, 108 move from collapsed to expanded configurations, but with a small degree of rotation than the proximal and/or distal transition sections.

Further, it is contemplated that only one of the proximal and distal transition sections 106, 108 may comprise the nested strut configuration wherein the nested strut configuration transition section may rotate slightly as described above and the central section 104 and non-nested transition section may, or may not, also rotate.

It is also contemplated that, in the case of the expandable region 102 comprising a stent structure, that the cell shape and/or size may not be uniform across the expandable region 102. For example, the proximal and/or distal transition sections 106, 108 may comprise a cell structure of a number, size and shape that differs from the cell structure number, size and shape of the central region 104. In one embodiment, the proximal and/or distal transition sections 106, 108 may comprise smaller cells than the expandable central section 104 and in another embodiment the central region 104 may comprise smaller cells than the transition sections 106, 108.

In the preferred embodiment it will now be apparent that to achieve the minimum diameter after collapsing that each adjacent connecting structure 132 will have the same or similar shape to maximize the nesting process.

The terms "nest", "nested" or "nesting" are defined herein to mean that the connecting structures 130 are shaped and arranged such that they can be in very close and complementary proximity when the expanded region is in the collapsed or delivery configuration and are separated and/or spaced apart from, and/or without substantial contact, with each other when in the expanded or working configuration.

It will now be apparent that in the case of a device comprising stent cells in the proximal and distal transition sections 106, 108 may not necessarily also comprise stent cells in the central expandable section 104. This central section 104 may comprise an expandable material and, because of the biasing forces provided by the transitions sections, may expand concomitantly with the transition sections without also specifically comprising a biasing expansion force. Thus, the biasing force of the transition sections 106, 108 may force the central section 104 to expand, which may comprise interwoven or interconnected wires or other structure that may form cells or other expandable material, e.g., a polymer including but not limited to a polymer jacket or sleeve, and that can move between collapsed and expanded configurations but that is not biased to expand or collapse. Alternatively, the central section 104 may also be biased to expand, with a comparable biasing force, with a greater biasing force or with a lesser biasing force than the biasing force of the transition regions 106, 108.

Turning now to FIGS. 16-19, an exemplary method for collapsing and expanding the device 100 is provided. Thus, in FIG. 16, the expandable region 102 is fully expanded and undeformed, just before introduction into the lumen of introducer sheath or delivery catheter 200. Note the exemplary expanded diameter of the expandable region 102 is between 16-20 Fr while the inner diameter of the introducer sheath lumen is indicated as 10 Fr. These are exemplary dimensions and may comprise other diameters as required.

Figure 17:
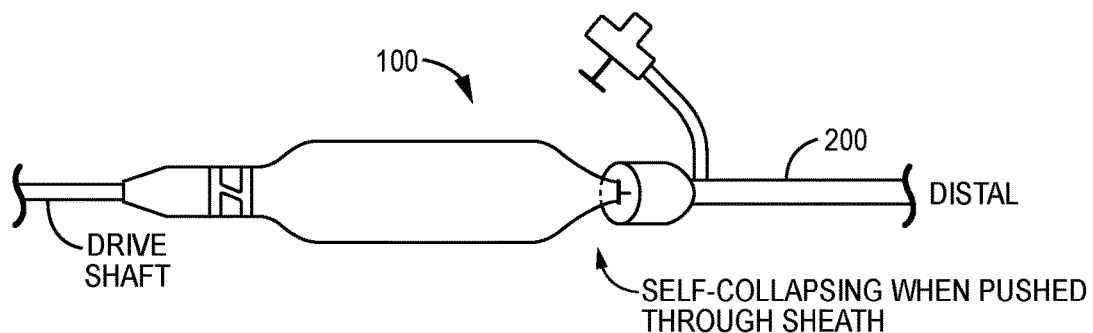
FIG. 17 is a side cutaway view of one embodiment of the present invention.
Figure 18:
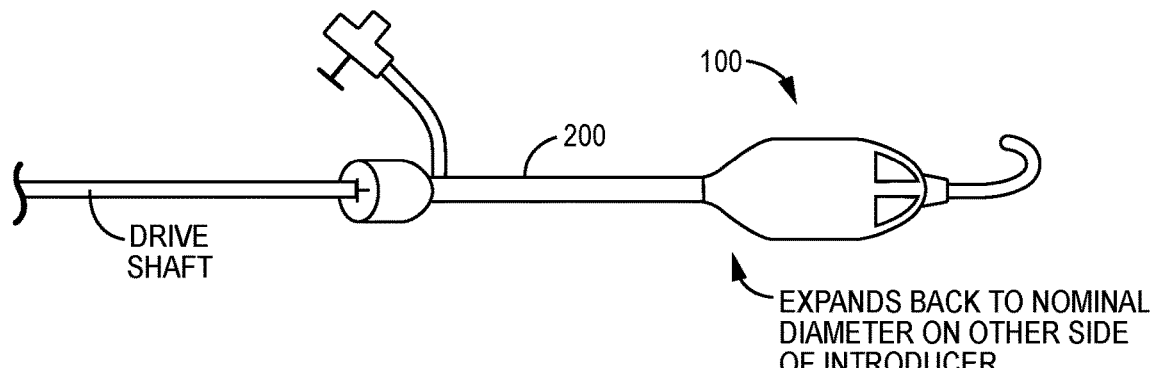
FIG. 18 is a side cutaway view of one embodiment of the present invention.
Figure 19:
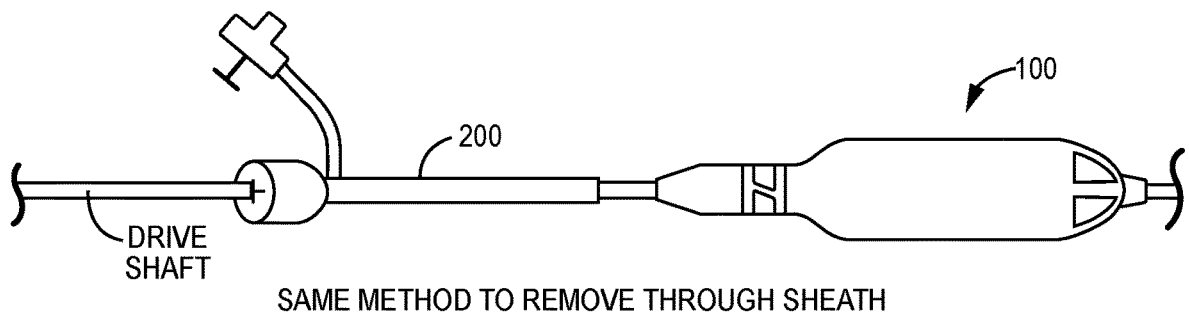
FIG. 19 is a side cutaway view of one embodiment of the present invention.

FIG. 17 continues with the guide wire and the distal end of expandable region 102 of device 100 being advanced into the lumen of introducer sheath 200, where the expandable region 102 begins to be compressed to adapt to the lumen's diameter. Ultimately, the entire expandable region 102 will be compressed and deformed within the introducer sheath's lumen to achieve a compressed, collapsed delivery configuration and translated along the lumen to the distal end of the lumen where it is pushed out of the lumen. Thus, in FIG. 18 the distal portion of the expandable region 102 is illustrated as at least partially expanded while the remaining more proximal portions of expandable region 102 remain compressed with lumen of introducer sheath 200. The axial translation of the device 100 and expandable region 102 continues until the expandable region 102 is completely released from the distal end of the introducer sheath lumen and, due to its biased expansion properties discussed herein, regains an expanded and working configuration.

The skilled artisan will now recognize the utility in transition section(s) 106, 108 in providing a mechanism for smoothly and easily compressing expandable region 102 to fit within the introducer sheath lumen and for providing a compressed diameter that is as small as possible and highly predictable due to the complementary nature of the connecting structures 132.

The above steps are simply reversed when the procedure is complete by pulling the device 100 and expandable region 102 proximally into the lumen of introducer sheath 102.

Figure 14B:
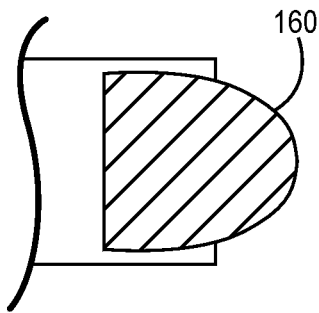
FIG. 14B is a side cutaway view of one embodiment of the present invention.
Figure 14C:
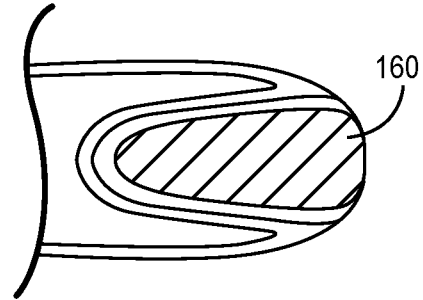
FIG. 14C is a side cutaway view of one embodiment of the present invention.

FIGS. 14A-14C provide a device 100 according to one of the embodiments discussed above and further comprising a self-opening cover 160 removably disposed over inlet apertures 12. As shown, the self-opening cover 160 may cover one or more of the inlet apertures 12 when the device 100 is not running and, therefore, not generating a vacuum through the device's lumen/flow channel as in FIG. 14B. When the device's motor (whether external to the patient or integrated with device) is actuated, a vacuum is generated within the flow channel of the device. Accordingly, as shown in FIG. 14C, the self-opening cover 160 is urged and pulled inward to open the inlet aperture(s) 12.

An alternate embodiment of a cover 170 is shown in FIGS. 15A and 15B. There, the inlet apertures are in FIG. 15A illustrated as covered by a cover 170 that is also connected with a distally positioned and axially translatable tip 172. When the axially translatable tip 172 is pushed distally the cover 170 moves to a contracted state, thereby exposing and opening the inlet apertures 12.

The description of the invention and its as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A motor-driven blood pump having a housing, inlet apertures, outlet apertures and further comprising:
   a pump assembly comprising at least a rotatable rotor within the housing;
   a collapsible and expandable region disposed distal of the pump assembly comprising a collapsible and expandable proximal transition section and a collapsible and expandable distal transition section, wherein the collapsible and expandable proximal and distal transition sections are biased to expand, and
   a central expandable region disposed between the collapsible and expandable proximal and distal transition sections, and
   wherein the central expandable region is not biased to expand and is adapted to expand as the collapsible and expandable proximal and distal transition sections biasingly expand; and
   a non-expandable regions disposed adjacent the proximal and distal sides of the collapsible and expandable region.

2. The blood pump of claim 1, wherein the collapsible and expandable proximal and distal transition sections region comprise a shape memory material or other material that expands and contracts.

3. The blood pump of claim 2, wherein the shape memory material comprises a metal and/or a polymer.

4. The blood pump of claim 1, wherein the central expandable region comprises a cylindrical or elliptical shape when expanded.

5. The blood pump of claim 1 wherein the collapsible and expandable proximal and distal transition sections comprise an expanded shape that differs from an expanded shape of the central expandable region.

6. The blood pump of claim 5, wherein the proximal and/or distal transition section comprise connecting structures connected with the central expandable region.

7. The blood pump of claim 6, wherein the collapsible and expandable proximal and distal transition sections comprise connecting structures with complementary geometric shapes.

8. The blood pump of claim 7, wherein the complementary geometric shapes of the connecting structures allow a nesting collapsing of the collapsible and expandable proximal and distal transition sections, whereby the blood pump comprises a delivery configuration.

9. The blood pump of claim 7, wherein the connecting structures comprise struts.

10. The blood pump of claim 5, wherein the central expandable region and expandable and collapsible proximal and/or distal transition section(s) comprise an expandable stent comprising a first stent cell pattern.

11. The blood pump of claim 5, wherein the central expandable region comprises an expandable stent comprising a first stent cell pattern and wherein the proximal and/or distal transition section(s) comprise an expandable stent having at least a second stent cell pattern that is different from the first stent cell pattern.

12. The blood pump of claim 1, wherein the collapsible and expandable region comprises a support structure comprising at least one of a stent structure and a polymer.

13. The blood pump of claim 1, further comprising a self-opening cover disposed over the inlet apertures of the device when the device's motor is not running, wherein the self-opening cover changes positions and uncovers the inlet apertures when the device's motor is running.

14. The blood pump of claim 1, further comprising an inlet aperture cover attached to an axially translatable tip and covering at least one inlet aperture, wherein distal translation of the axially translatable tip uncovers the at least one inlet aperture.

15. The blood pump of claim 1, further comprising a drive shaft operatively connected at a distal end with the pump assembly and with a prime mover operatively attached to a proximal end of the drive shaft.

* * * * *